(12) United States Patent
Bianchi et al.

(10) Patent No.: US 9,763,787 B2
(45) Date of Patent: Sep. 19, 2017

(54) ASSEMBLED IMPLANT

(75) Inventors: John R. Bianchi, Alachua, FL (US); C. Randal Mills, Alachua, FL (US); P. J. Gorham, Alachua, FL (US); Michael Esch, Alachua, FL (US); Kevin C. Carter, Alachua, FL (US); Pat Coleman, Alachua, FL (US); Kevin Ross, Alachua, FL (US); Harry W. Rambo, Alachua, FL (US); Darren G. Jones, Alachua, FL (US); Dayna Buskirk, Alachua, FL (US)

(73) Assignee: RTI Surgical, Inc., Alachua, FL (US)

( * ) Notice: Subject to any disclaimer, the term of this patent is extended or adjusted under 35 U.S.C. 154(b) by 0 days.

(21) Appl. No.: 12/690,074

(22) Filed: Jan. 19, 2010

(65) Prior Publication Data

US 2010/0268349 A1 Oct. 21, 2010

Related U.S. Application Data

(63) Continuation of application No. 09/782,594, filed on Feb. 12, 2001, now abandoned, which is a
(Continued)

(51) Int. Cl.
*A61F 2/28* (2006.01)
*A61L 2/00* (2006.01)
(Continued)

(52) U.S. Cl.
CPC .............. *A61F 2/28* (2013.01); *A61F 2/446* (2013.01); *A61F 2/447* (2013.01); *A61L 2/0088* (2013.01);
(Continued)

(58) Field of Classification Search
CPC A61F 2/4611; A61F 2/442; A61F 2220/0041; A61F 2310/00359; A61F 2/28;
(Continued)

(56) References Cited

U.S. PATENT DOCUMENTS

| 3,291,640 A | 12/1966 | Livingston |
| 4,193,818 A | 3/1980 | Young et al. |

(Continued)

FOREIGN PATENT DOCUMENTS

| EP | 0517030 | 5/1992 |
| WO | WO 9909914 | 3/1999 |

(Continued)

OTHER PUBLICATIONS

Translation from German European Patent Application EP-0517030 A2 published May 1992.*

(Continued)

*Primary Examiner* — Paul Prebilic
(74) *Attorney, Agent, or Firm* — McAndrews, Held and Malloy

(57) ABSTRACT

This invention is directed to an assembled implant comprising two or more portions of bone that are held together in appropriate juxtaposition with one or more biocompatible pins to form a graft unit. Preferably, the pins are cortical bone pins. Typically, the cortical pins are press-fitted into appropriately sized holes in the bone portions to achieve an interference fit. The bone portions are allograft or xenograft.

16 Claims, 14 Drawing Sheets

Related U.S. Application Data continuation-in-part of application No. 09/191,232, filed on Nov. 13, 1998, now Pat. No. 6,482,584, and a continuation-in-part of application No. 09/378,527, filed on Aug. 20, 1999, now Pat. No. 6,652,818, and a continuation-in-part of application No. 09/722,205, filed on Nov. 25, 2000, now Pat. No. 7,048,765, which is a continuation-in-part of application No. 08/920,630, filed on Aug. 27, 1997, now abandoned, said application No. 09/782,594 is a continuation-in-part of application No. 09/390,174, filed on Sep. 7, 1999, now Pat. No. 6,613,278, and a continuation-in-part of application No. 29/123,227, filed on May 12, 2000, now Pat. No. Des. 461,248.

(60) Provisional application No. 60/181,622, filed on Feb. 10, 2000.

(51) Int. Cl.
*A61L 2/025* (2006.01)
*A61F 2/08* (2006.01)
*A61F 2/30* (2006.01)
*A61F 2/44* (2006.01)
*A61F 2/46* (2006.01)

(52) U.S. Cl.
CPC .............. *A61L 2/025* (2013.01); *A61F 2/08* (2013.01); *A61F 2/0811* (2013.01); *A61F 2/3094* (2013.01); *A61F 2/442* (2013.01); *A61F 2/4644* (2013.01); *A61F 2002/2817* (2013.01); *A61F 2002/2835* (2013.01); *A61F 2002/2839* (2013.01); *A61F 2002/3028* (2013.01); *A61F 2002/30057* (2013.01); *A61F 2002/30059* (2013.01); *A61F 2002/30062* (2013.01); *A61F 2002/3085* (2013.01); *A61F 2002/30113* (2013.01); *A61F 2002/30153* (2013.01); *A61F 2002/30179* (2013.01); *A61F 2002/30224* (2013.01); *A61F 2002/30225* (2013.01); *A61F 2002/30235* (2013.01); *A61F 2002/30261* (2013.01); *A61F 2002/30266* (2013.01); *A61F 2002/30329* (2013.01); *A61F 2002/30354* (2013.01); *A61F 2002/30383* (2013.01); *A61F 2002/30387* (2013.01); *A61F 2002/30448* (2013.01); *A61F 2002/30492* (2013.01); *A61F 2002/30563* (2013.01); *A61F 2002/30599* (2013.01); *A61F 2002/30677* (2013.01); *A61F 2002/30785* (2013.01); *A61F 2002/30795* (2013.01); *A61F 2002/30904* (2013.01); *A61F 2002/30957* (2013.01); *A61F 2002/30975* (2013.01); *A61F 2002/4649* (2013.01); *A61F 2210/0004* (2013.01); *A61F 2220/005* (2013.01); *A61F 2220/0025* (2013.01); *A61F 2220/0033* (2013.01); *A61F 2230/0006* (2013.01); *A61F 2230/0019* (2013.01); *A61F 2230/0058* (2013.01); *A61F 2230/0063* (2013.01); *A61F 2230/0069* (2013.01); *A61F 2230/0082* (2013.01); *A61F 2250/0063* (2013.01); *A61F 2310/0097* (2013.01); *A61F 2310/00365* (2013.01); *A61F 2310/00383* (2013.01); *A61F 2310/00976* (2013.01)

(58) Field of Classification Search
CPC .... A61F 2002/30062; A61F 2201/0004; A61F 2002/2817; A61F 2002/2835; A61F 2002/2839; A61F 2210/0004; A61L 27/12
USPC .......... 623/17.11, 17.16, 23.51, 23.56, 23.63
See application file for complete search history.

(56) References Cited

U.S. PATENT DOCUMENTS

| | | | | |
|---|---|---|---|---|
| 4,294,753 | A | 10/1981 | Urist | |
| 4,828,563 | A | 5/1989 | Muller-Lierheim | |
| 4,872,840 | A * | 10/1989 | Bori ........................ | A61C 3/16 433/173 |
| 4,950,296 | A | 8/1990 | McIntyre | |
| 4,969,909 | A | 11/1990 | Barouk | |
| 5,037,437 | A | 8/1991 | Matsen | |
| 5,084,051 | A | 1/1992 | Tormala et al. | |
| 5,112,354 | A | 5/1992 | Sires | |
| 5,147,367 | A | 9/1992 | Ellis | |
| 5,180,388 | A | 1/1993 | DiCarlo | |
| 5,192,327 | A | 3/1993 | Brantigan | |
| 5,213,619 | A | 5/1993 | Jackson | |
| 5,281,422 | A | 1/1994 | Badylak | |
| 5,288,462 | A | 2/1994 | Carter | |
| 5,298,222 | A | 3/1994 | O'Leary | |
| 5,329,846 | A | 7/1994 | Bonutti | |
| 5,333,626 | A | 8/1994 | Morse | |
| 5,380,826 | A | 1/1995 | Castor | |
| 5,429,810 | A | 7/1995 | Knaepler | |
| 5,437,287 | A | 8/1995 | Phillips | |
| 5,460,962 | A | 10/1995 | Kemp | |
| 5,507,813 | A | 4/1996 | Dowd et al. | |
| 5,509,968 | A | 4/1996 | Carr | |
| 5,513,662 | A | 5/1996 | Morse | |
| 5,545,222 | A | 8/1996 | Bonutti | |
| 5,556,379 | A | 9/1996 | Wolfinbarger | |
| 5,571,190 | A | 11/1996 | Ulrich et al. | |
| 5,626,861 | A | 5/1997 | Laurencin et al. | |
| 5,658,882 | A | 8/1997 | Celeste | |
| 5,674,286 | A | 10/1997 | D'Alessio et al. | |
| 5,674,292 | A | 10/1997 | Tucker | |
| 5,676,700 | A | 10/1997 | Black et al. | |
| 5,711,921 | A | 1/1998 | Langford | |
| 5,716,358 | A | 2/1998 | Ochoa et al. | |
| 5,716,454 | A | 2/1998 | Carr | |
| 5,723,012 | A | 3/1998 | Fages | |
| 5,725,579 | A | 3/1998 | Fages | |
| 5,753,195 | A | 5/1998 | Langford | |
| 5,785,966 | A | 7/1998 | Coles | |
| 5,797,871 | A | 8/1998 | Wolfinbarger | |
| 5,814,084 | A | 9/1998 | Grivas et al. | |
| 5,846,484 | A | 12/1998 | Scarborough | |
| 5,861,041 | A | 1/1999 | Tienboon | |
| 5,865,848 | A | 2/1999 | Baker | |
| 5,899,939 | A | 5/1999 | Boyce et al. | |
| 5,944,755 | A | 8/1999 | Stone | |
| 5,989,289 | A | 11/1999 | Coates et al. | |
| 5,993,844 | A | 11/1999 | Abraham | |
| 6,024,735 | A | 2/2000 | Wolfinbarger | |
| 6,025,538 | A | 2/2000 | Yaccarino, III | |
| 6,027,743 | A | 2/2000 | Khouri | |
| 6,090,998 | A | 7/2000 | Grooms et al. | |
| 6,102,056 | A | 8/2000 | Kotsopey | |
| 6,123,731 | A | 9/2000 | Boyce et al. | |
| 6,146,420 | A | 11/2000 | McKay | |
| 6,149,864 | A | 11/2000 | Dillow | |
| 6,200,347 | B1 | 3/2001 | Anderson et al. | |
| 6,206,931 | B1 | 3/2001 | Cook | |
| 6,258,125 | B1 * | 7/2001 | Paul et al. ................. | 623/17.11 |
| 6,371,988 | B1 * | 4/2002 | Pafford et al. ............ | 623/17.11 |
| 6,379,385 | B1 | 4/2002 | Kalas et al. | |
| 6,398,786 | B1 | 6/2002 | Sesic | |
| 6,402,783 | B1 | 6/2002 | Stone | |
| 6,482,584 | B1 | 11/2002 | Mills et al. | |
| 6,494,883 | B1 | 12/2002 | Ferree | |
| 6,497,726 | B1 | 12/2002 | Carter et al. | |
| 6,554,863 | B2 | 4/2003 | Paul et al. | |
| 6,613,278 | B1 | 9/2003 | Mills | |
| 6,652,818 | B1 | 11/2003 | Mills et al. | |
| 6,719,794 | B2 * | 4/2004 | Gerber et al. ............. | 623/17.11 |

(56) References Cited

U.S. PATENT DOCUMENTS

| | | | |
|---|---|---|---|
| 6,761,738 B1 | 7/2004 | Boyd | |
| 6,761,739 B2 | 7/2004 | Shepard | |
| 6,805,713 B1 | 10/2004 | Carter et al. | |
| 6,855,167 B2 | 2/2005 | Shimp et al. | |
| 6,893,462 B2 | 5/2005 | Buskirk et al. | |
| 6,986,788 B2 | 1/2006 | Paul et al. | |
| 7,115,146 B2* | 10/2006 | Boyer et al. | 623/23.63 |
| 7,300,464 B2 | 11/2007 | Tran | |
| 7,300,465 B2 | 11/2007 | Paul et al. | |
| 7,309,356 B2 | 12/2007 | Steiner | |
| 7,347,873 B2 | 3/2008 | Paul et al. | |
| 8,075,622 B2* | 12/2011 | Van Hoeck et al. | 623/17.16 |
| 2001/0008979 A1 | 7/2001 | Bonutti | |
| 2001/0039458 A1 | 11/2001 | Boyer et al. | |
| 2001/0041941 A1 | 11/2001 | Boyer, II et al. | |
| 2003/0023304 A1 | 1/2003 | Carter et al. | |
| 2003/0027125 A1 | 2/2003 | Hanstke et al. | |
| 2003/0036800 A1 | 2/2003 | Meredith | |
| 2003/0077825 A1 | 4/2003 | Bhatnagar et al. | |
| 2003/0097179 A1 | 5/2003 | Carter et al. | |
| 2003/0105528 A1 | 6/2003 | Shimp et al. | |
| 2003/0125755 A1 | 7/2003 | Drews et al. | |
| 2005/0025667 A1 | 2/2005 | Christensen et al. | |
| 2005/0065607 A1 | 3/2005 | Gross | |
| 2005/0096742 A1 | 5/2005 | Mills et al. | |
| 2005/0100862 A1 | 5/2005 | Mills et al. | |
| 2006/0106460 A1 | 5/2006 | Messerli et al. | |
| 2006/0200235 A1 | 9/2006 | Bianchi et al. | |
| 2006/0200236 A1 | 9/2006 | Bianchi et al. | |
| 2006/0212036 A1 | 9/2006 | Bianchi et al. | |
| 2006/0241763 A1 | 10/2006 | Paul et al. | |
| 2007/0016295 A1 | 1/2007 | Boyd | |

FOREIGN PATENT DOCUMENTS

| | | |
|---|---|---|
| WO | WO 99/38543 | 8/1999 |
| WO | WO 0029037 | 5/2000 |
| WO | WO 0040177 | 7/2000 |
| WO | WO 0054821 | 9/2000 |
| WO | WO 0108715 | 2/2001 |
| WO | WO 0178798 | 10/2001 |

OTHER PUBLICATIONS

Non-provisional U.S. Appl. No. 08/920,630, filed Aug. 27, 1997.*
Albee, "Bone Surgery with Machine Tools", Scientific American, (154(4): 178-181 (Apr. 1936).
Gie, et al. "Contained Morselized Allograft in Revision Total HIP Arthroplasty", Orthopedic Clinics of North America: 717-725, vol. 24, No. 4, United Kingdom (1993).
Communication Pursuant to Article 94(3) EPC corresponding to European Patent Application No. 01 968 600.5-1219, dated Jul. 8, 2010.
EPO, Communication, "Result of Consultation" with Drawing for Appln. No. 01916085.2, dated Sep. 25, 2008.
EPO, Summons to Attend Oral Proceedings Pursuant to Rule 115(1)EPC with Annex to the communication (pp. 1-3) for Appln. No. 01916085.2, dated Apr. 23, 2008.
EPO, Communication Pursuant to Article 96(2) EPC with Annex to the communication (pp. 1-3) for Appln. No. 01916085.2, dated Jul. 14, 2006.
EPO, Communication Pursuant to Article 96(2) EPC with Annex to the communication (pp. 1-2) for Appln. No. 01916085.2, dated Oct. 19, 2004.
EPO, Communication Pursuant to Article 94(3) EPC with Annex to the communication (pp. 1-5) for Appln. No. 01968600.5, dated May 2, 2008.
EPO, Communication Pursuant to Article 96(2) EPC with Annex to the communication (pp. 1-6) for Appln. No. 01968600.5, dated Apr. 18, 2005.
EPO, Communication Pursuant to Article 96(2) EPC with Annex to the communication (p. 1) for Appln. No. 01968600.5, dated Aug. 17, 2004.
Merriam-Webster OnLine defintions for allograft http://www.m-w.com/cgi-bin/dictionary?book+Dictionary&va=allograft (Feb. 21, 2006).
Merriam-Webster OnLine defintions for allograft http://www.m-w.com/cgi-bin/dictionary?book+Dictionary&va=allogenic (Feb. 21, 2006)
Stedman's Medical Dictionary, The Williams & Wilkins Company, 23rd Edition, (c) 1976, p. 599.
CIPO, Requisition by Examiner, for Appln. No. 2,437,763, dated Jun. 26, 2009.
JPO, translation of Notice of Final Rejection, for Application No. 2002-563972, dated Feb. 27, 2007.
Decision on Appeal, for U.S. Appl. No. 10/387,322, dated Apr. 14, 2009, (pp. 1-14).
Examiner's Answer, for U.S. Appl. No. 10/387,322, dated Oct. 19, 2007, (pp. 1-7).
Advisory Action Before the filing of an Appeal Brief, for U.S. Appl. No. 10/387,322, dated Feb. 3, 2006 (pp. 1-3).
Office Action, for U.S. Appl. No. 10/387,322, dated Nov. 22, 2005 (pp. 1-6).
Office Action, for U.S. Appl. No. 10/387,322, dated Aug. 1, 2005 (pp. 1-6).
Office Action, for U.S. Appl. No. 10/387,322, dated Jun. 20, 2005 (pp. 1-9).
Office Action, for U.S. Appl. No. 10/387,322, dated Dec. 7, 2004 (pp. 1-7).
Office Action, for U.S. Appl. No. 10/387,322, dated Jul. 30, 2004 (pp. 1-7).
Office Action, for U.S. Appl. No. 09/941,154, dated Jan. 31, 2008 (pp. 1-9).
Office Action, for U.S. Appl. No. 09/941,154, dated May 18, 2007 (pp. 1-9).
Interview Summary, for U.S. Appl. No. 09/941,154, dated May 7, 2007 (pp. 1-9).
Office Action, for U.S. Appl. No. 09/941,154, dated Oct. 31, 2006 (pp. 1-9).
Office Action, for U.S. Appl. No. 09/941,154, dated Jan. 11, 2006 (pp. 1-11).
Office Action, for U.S. Appl. No. 09/941,154, dated Aug. 1, 2005 (pp. 1-6).
Decision on Appeal, for U.S. Appl. No. 09/782,594, dated Nov. 16, 2009 (pp. 1-14).
Examiner's Answer, for U.S. Appl. No. 09/782,594, dated Dec. 22, 2008 (pp. 1-9).
Office Action, for U.S. Appl. No. 09/782,594, dated Apr. 4, 2008 (pp. 1-9).
Office Action, for U.S. Appl. No. 09/782,594, dated May 3, 2007 (pp. 1-12).
Office Action, for U.S. Appl. No. 09/782,594, dated Oct. 25, 2006 (pp. 1-11).
Office Action, for U.S. Appl. No. 09/782,594, dated Feb. 27, 2006 (pp. 1-9).
Office Action, for U.S. Appl. No. 09/782,594, dated Sep. 27, 2005 (pp. 1-8).
Office Action, for U.S. Appl. No. 09/782,594, dated Mar. 24, 2005 (pp. 1-9).
Advisory Action, for U.S. Appl. No. 09/782,594, dated Jan. 4, 2005 (pp. 1-3).
Advisory Action, for U.S. Appl. No. 09/782,594, dated Dec. 8, 2004 (pp. 1-3).
Office Action, for U.S. Appl. No. 09/782,594, dated Jul. 23, 2004 (pp. 1-7).
Office Action, for U.S. Appl. No. 09/782,594, dated Nov. 4, 2003 (pp. 1-9).
Office Action, for U.S. Appl. No. 09/782,594, dated Jul. 31, 2003 (pp. 1-6).

* cited by examiner

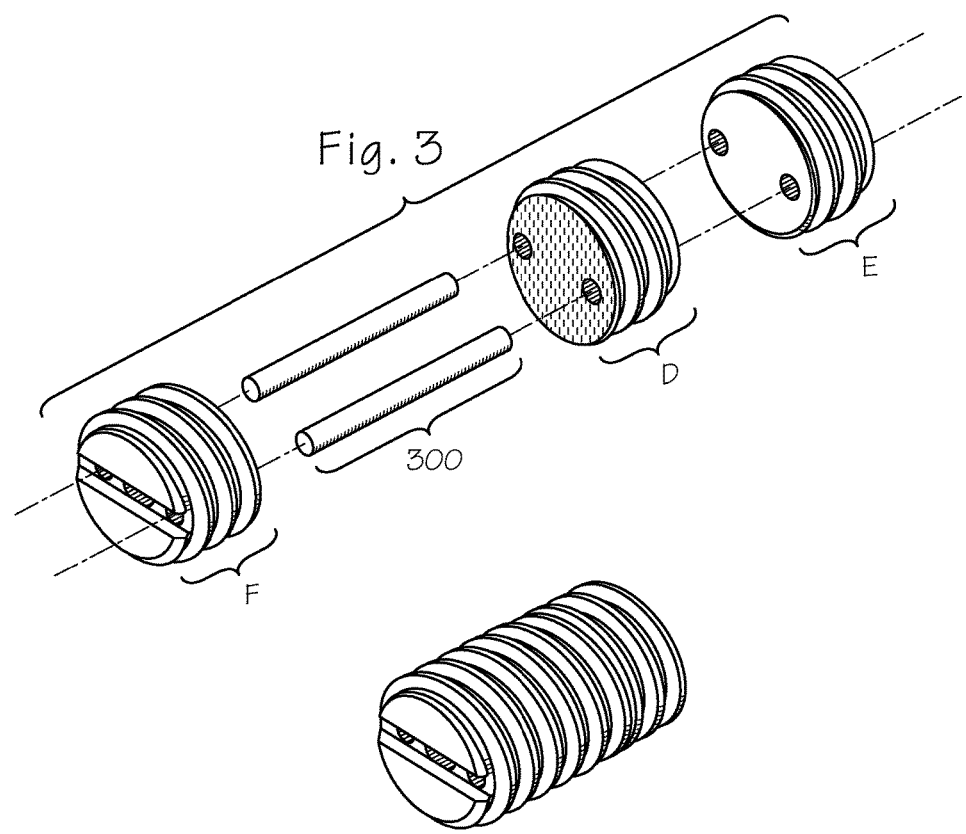
Fig. 3
Fig. 4
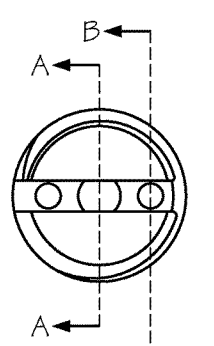
Fig. 5
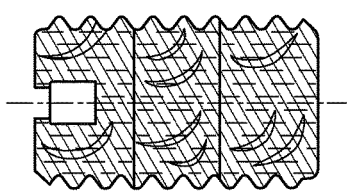
Fig. 6
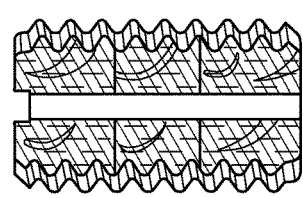
Fig. 7

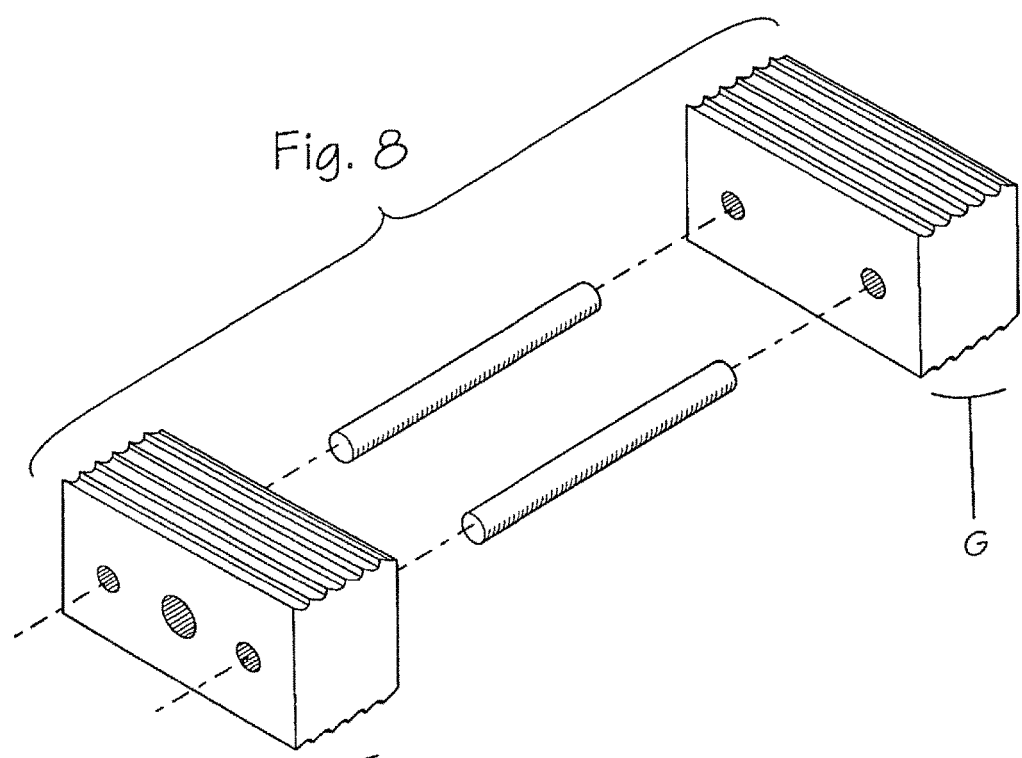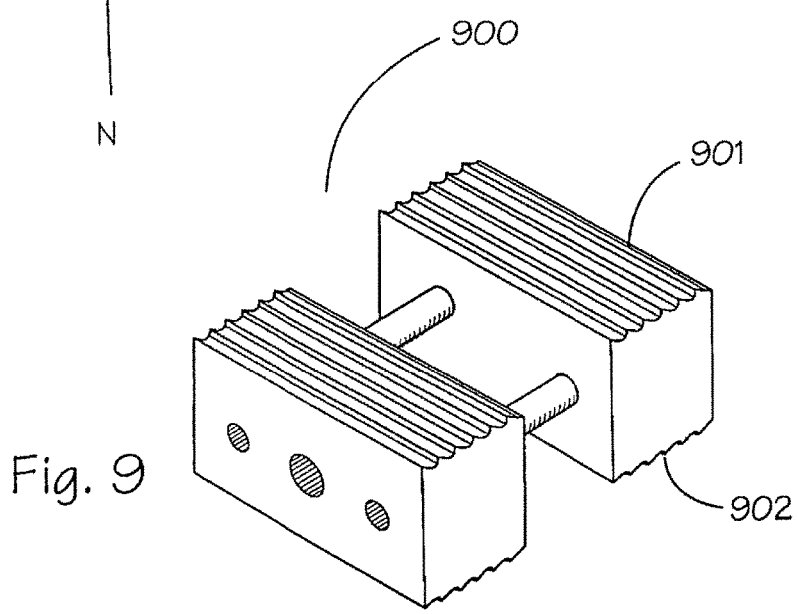

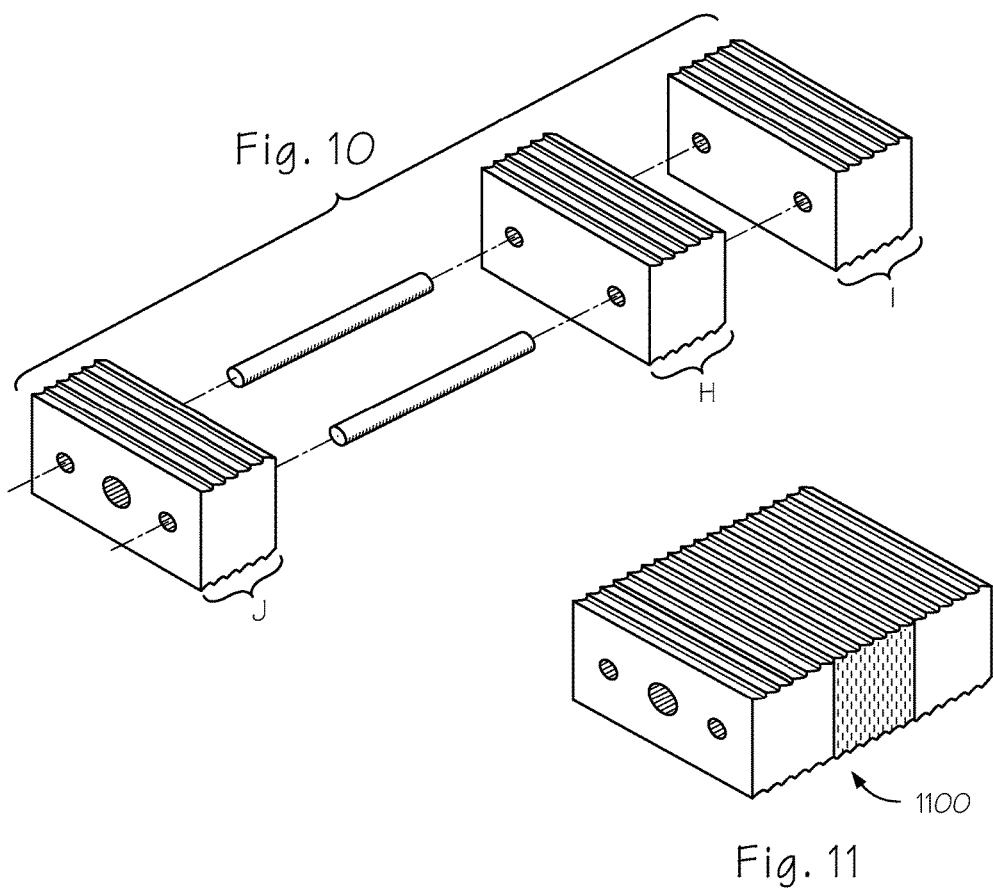
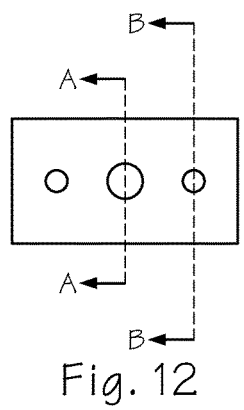
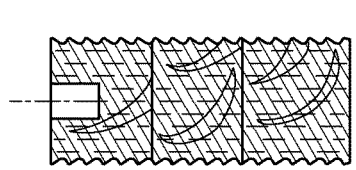
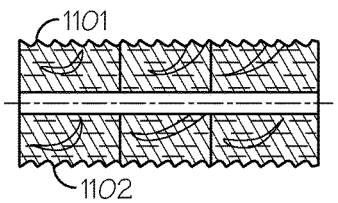
Fig. 10
Fig. 11
Fig. 12
Fig. 13
Fig. 14

2000

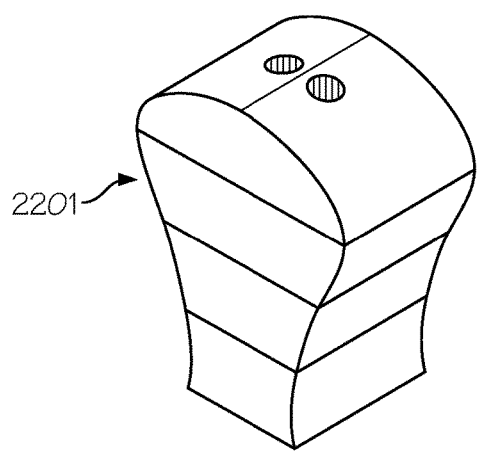
Fig. 22A
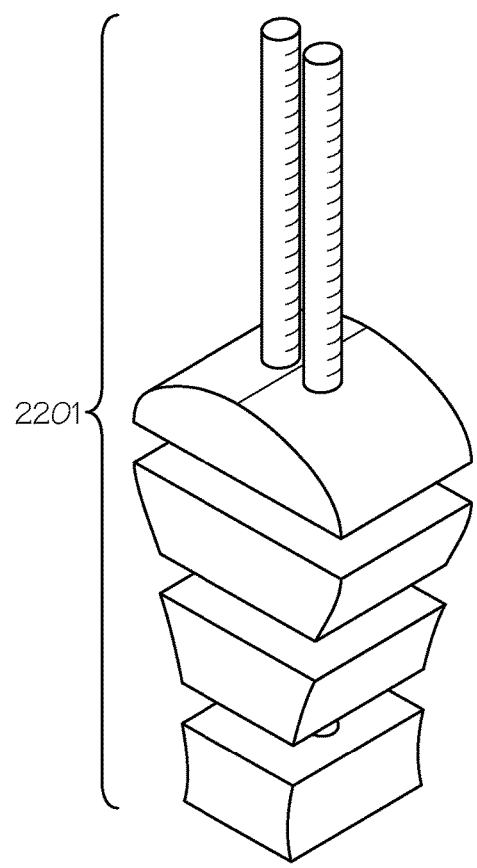
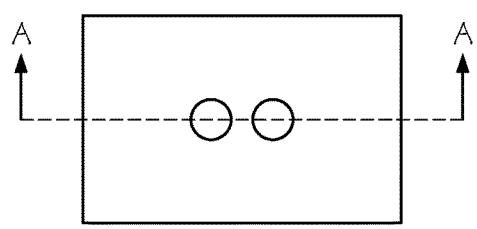
Fig. 22C
Fig. 22B
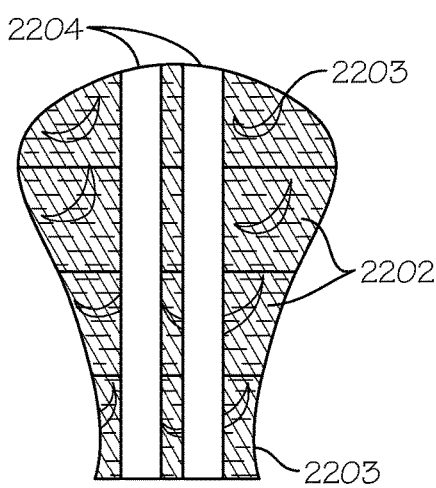
Fig. 22D
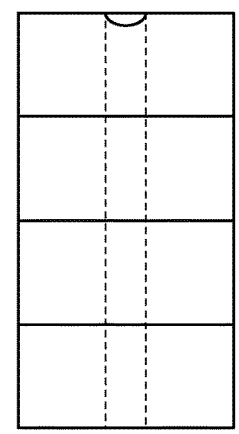
Fig. 22E

ASSEMBLED IMPLANT

CROSS REFERENCE TO RELATED APPLICATION

This application is a continuation of Ser. No. 09/782,594 filed Feb. 12, 2001, now abandoned, which claims benefit of 60/181,622 filed Feb. 10, 2000 and said Ser. No. 09/782,594 is a continuation-in-part of each of the following: U.S. application Ser. No. 09/191,232 filed on Nov. 13, 1998, now U.S. Pat. No. 6,482,584; U.S. application Ser. No. 09/378,527, filed on Aug. 20, 1999, now U.S. Pat. No. 6,652,818; U.S. application Ser. No. 09/722,205, filed Nov. 25, 2000, now U.S. Pat. No. 7,048,765, which is a continuation-in-part of U.S. application Ser. No. 08/920,630, filed Aug. 27, 1997, now abandoned; U.S. application Ser. No. 09/390,174, filed on Sep. 7, 1999, now U.S. Pat. No. 6,613,278; and of U.S. application Ser. No. 29/123,227, filed on May 12, 2000, now U.S. Design Pat. D461,248; the priority of all of which is claimed herein under 35 U.S.C. §120.

FIELD OF THE INVENTION

This invention relates to implants and methods for their preparation wherein components of the implant are assembled from constituent pieces to produce a complete implant.

BACKGROUND OF THE INVENTION

In the field of medicine, there has been an increasing need to develop implant materials for correction of biological defects. Particularly in the field of orthopedic medicine, there has been the need to replace or correct bone, ligament and tendon defects or injuries. As a result, there have emerged a number of synthetic implant materials, including but not limited to metallic implant materials and devices, devices composed in whole or in part from polymeric substances, as well as allograft, autograft, and xenograft implants. It is generally recognized that for implant materials to be acceptable, they must be pathogen-free, and must be biologically acceptable. Generally, it is preferable if the implant materials may be remodeled over time such that autogenous bone replaces the implant materials. This goal is best achieved by utilizing autograft bone from a first site for implantation into a second site. However, use of autograft materials is attended by the significant disadvantage that a second site of morbidity must be created to harvest autograft for implantation into a first diseased or injured site. As a result, allograft and xenograft implants have been given increasing attention in recent years. However, use of such materials has the disadvantage that human allograft materials are frequently low in availability and are high in cost of recovery, treatment and preparation for implantation. By contrast, while xenograft implant materials, such as bovine bone, may be of ready availability, immunological and disease transmission considerations imply significant constraints on the ready use of such materials.

In view of the foregoing considerations, it remains the case that there has been a long felt need for unlimited supplies of biologically acceptable implant materials for repair of bone and other defects or injuries. This invention provides a significant advance in the art, and largely meets this heed, by providing materials and methods for production of essentially any form of implant from component parts to produce assembled implants.

In recent months, there have appeared several patents and patent publications which address similar or identical considerations to those to which the present invention disclosure is directed. Specifically, reference is made to PCT publication WO00/40177, which published on 13 Jul. 2000, the disclosure of which is hereby incorporated by reference as if fully set forth herein.

In addition, reference is made herein to U.S. Pat. No. 5,899,939 to Boyce, which issued on May 4, 1999, the disclosure of which is hereby incorporated by reference as if fully set forth herein.

Finally, reference is made herein to U.S. Pat. No. 6,025,538 to Yaccarino, which issued on Feb. 15, 2000, the disclosure of which is hereby incorporated by reference as if fully set forth herein.

SUMMARY OF THE INVENTION

This invention provides a method for manufacture of autograft, allograft and xenograft implants which comprises assembling such implants from smaller pieces of graft materials to form a larger graft implant product.

Accordingly, it is one object of this invention to provide a method for assembly of multiple bone implant shapes from smaller bone implant pieces.

Another object of this invention is to provide assembled bone implants.

Another object of this invention is to provide a method whereby otherwise wasted tissue may be used in the production of useful orthopedic implants.

Further objects and advantages of this invention will be appreciated from a review of the complete disclosure and the appended claims.

BRIEF DESCRIPTION OF THE DRAWINGS

Attached to this invention disclosure are a large number of sketches which demonstrate a wide variety of assembled implants which may be prepared and used according to this invention.

FIG. 3 provides a schematic of an assembled implant according to this invention.

FIGS. 4-7 provides a schematic of an assembled implant according to this invention.

FIGS. 8-9 provides a schematic of an assembled implant according to this invention.

FIGS. 10-14 provides a schematic of an assembled implant according to this invention.

FIG. 22 provides a schematic of an assembled implant according to this invention.

DETAILED DESCRIPTION OF THE PREFERRED EMBODIMENTS

Figure 1:
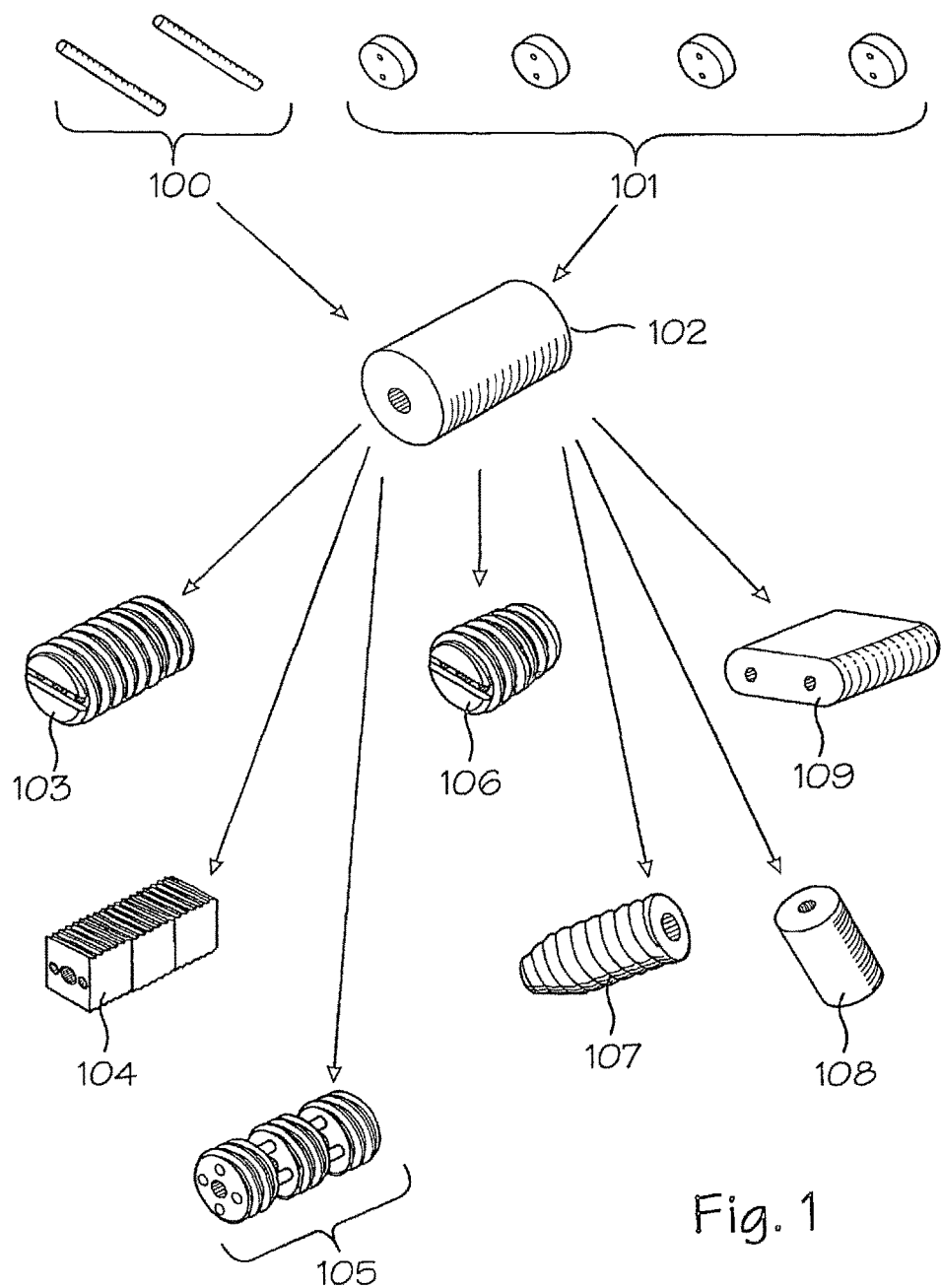
FIG. 1 is a flow chart showing the formation of various sub-component parts of an assembled implant according to this invention, from which assembled implants and a kit comprising these parts may be formed according to the disclosure of this invention.

Currently, autograft, allograft and xenograft products are produced as solid, continuous materials. For example, bone dowels (see U.S. Pat. No. 5,814,084, hereby incorporated by reference), Smith-Robinson cervical spine implants, iliac crest grafts, and the like are harvested and machined from single, continuous pieces of bone. The present invention provides methods for manufacture of autograft, allograft and xenograft implants by assembling such implants from smaller pieces of graft materials to form a larger graft implant product. As a result, increased utilization of valuable implant materials is achieved, thereby more effectively meeting the ever-increasing demands for graft implant materials. In addition, greater flexibility is achieved in the types and shapes of implant materials is achieved. Essentially, any implant piece that may be required may be formed according to the present invention, and orthopedic surgeons may be provided with kits of assemblable parts which may be formed in the course of a surgical procedure to precisely meet the needs of a given patient or procedure. In yet another aspect of this invention, existing graft products may be strengthened or reinforced by assembly of different types of graft materials into an assembled product. One example of such a reinforced product is a cancellous wedge, block, dowel or the like into which is inserted reinforcing pins of cortical bone. As a result, those skilled in the art will understand from this disclosure that different sections of tissue may be assembled to make a complete graft implant. Furthermore, this invention provides for the product of assembled implants comprising any one or combinations of allograft materials, autograft materials, xenograft materials, synthetic materials, metallic materials and the like. Furthermore, the assembled implants or the component pieces which are combined to form the assembled implant may be pre-treated or treated after assembly to incorporate any desired biologically active or inert materials. Thus, for example, in an assembled bone dowel implant according to this invention, the assembled bone dowel comprises segments of cortical bone pinned to each other by means of cortical bone pins. Prior to assembly or after assembly, the graft materials are soaked, infused, impregnated, coated or otherwise treated with bone morphogenetic proteins (BMP's), antibiotics, growth factors, nucleic acids, peptides, and the like.

It will be appreciated that variously shaped wafers, blocks, rings, washer-shaped bone pieces and the like may be affixed to each other in any secure and biologically acceptable manner. Preferably, the assembled pieces of bone are affixed to each other by means of pins, screws, rods, interference fit, threaded fits, key-way fit, and the like made from cortical bone. These fixation pieces are machined in a CNC lathe or the like to appropriate dimensions and are then threaded into mating holes tapped in the pieces to be assembled, or are pressed into drilled holes through adjacent pieces to be assembled by a pneumatic press or the like. In this fashion, very strong and tightly fitted pieces of implant materials may be joined and implanted. The assembled pieces may first be machined to desired dimensions and shapes, prior to assembly, the assembled implant may be machined, or both.

As noted above, the implant according to this invention may comprise an assembled cancellous block, dowel or the like, harvested from the iliac crest or another suitable site. As is known in the art, due to the wafer-like structure of cancellous bone, such grafts have low load-bearing characteristics. There exist reports in the literature of instances of extrusion, expulsion or collapse of iliac crest wedges, Cloward Dowels, and the like when utilized, for example, in spinal fusions. Nonetheless, use of cancellous bone is preferable over use of cortical bone implants, since cancellous bone is more osteoconductive than cortical bone. According to this invention, a Cloward Dowel, iliac crest wedge, or cancellous bone block, dowel or the like is reinforced by insertion therein of cortical bone pins. According to the method of this invention, cortical implants may also be reinforced by insertion therein of cortical bone pins, including when an assembled implant is prepared comprising different segments of cortical bone, cancellous bone or both. Insertion of the reinforcing pins provides an implant with multiple load-bearing pillars. The pins may be made to protrude from the surface of the implant to engage with inferior, superior or both surfaces of bone between which the implant is inserted. Thus, in a spinal implant, pin protrusions may be employed to created contact between the implant and the vertebral bodies, thus preventing extrusion and reinforcing a secure fit of the implant between adjacent vertebrae. We have, surprisingly, found that cortical pins of about 4.5 mm in diameter may each support a load of up about 2700 newtons (160 Mpa). Thus, according to the method of this invention, multiple pins may be inserted into an implant to produce a load-bearing capacity of known proportions (e.g. 10,000 newtons by insertion of five pins).

A further advantage of this invention is that it permits use of tissues that are not currently amenable to standard autograft, allograft or xenograft harvesting and processing procedures, such as ribs, metatarsal bone and the like. In addition, useful implant materials may be harvested and produced from otherwise un-useable donor tissues. In addition, due to the different nature of various segments of bone that are incorporated into the assembled, reinforced implants of this invention, various shaping methods aside from CNC lathe or other known procedures may be applied to different segments of the implant. Thus, a cancellous portion of bone implant may be compression molded, and then affixed to other portions of cortical or cancellous bone machined according to different or similar principles. In addition, due to the ability provided by this invention to assemble implant pieces, implants of unusual sizes and dimensions may be prepared and machined. Thus, implants of 100 mm in size could be machined, for example, for corpectomies, when otherwise bone stock for manufacture of such implant dimensions would not be available.

In view of the present disclosure, it will be appreciated that this invention provides a wide variety of assembled implants and implant parts: dowel shaped implants comprising assembled dowel segments, between about two to about ten segments, pinned together by one or more cortical bone pins. The assembled segments may closely abut each other or may be spread apart from each other. Such implants may be prepared by harvesting disks of cortical bone, drilling and optionally tapping holes therein, and inserting shafts of cortical pins therethrough, or therein, optionally by threading portions thereof for torquing into optionally tapped holes. The thus produced dowels may be tapered or have parallel sides. In addition, dowels which are harvested as a cross-section across the intramedullary canal of a long bone, as in U.S. Pat. No. 5,814,084, which might otherwise not pass production specifications, due to penetration of one outside wall into the intramedullary canal, may be completed by insertion therein of a cortical pin. Likewise, where a sidewall is otherwise considered to be too narrow, a "doughnut" of bone may be affixed to the sidewall by means of a cortical pin. A longer dowel may be prepared by affixing two dowels to each other. A posterior longitudinal interbody fusion implant (PLIF) may be machined from a single piece of cortical bone, or be assembled from two pieces of bone which are affixed to each other by means of a cortical pin. A bone screw may also be prepared according to the method of this invention by affixing multiple pieces of cortical bone to each other with a cortical bone pin, and then machining a thread on the exterior of the assembled bone pieces. It will further be appreciated from this disclosure that different portions of the assembled implant may be demineralized, to achieve a level of elasticity or compressibility not otherwise present in cortical or cancellous bone. Different portions of bone may also be retained on a shaft by means of a cotter-pin type device.

In addition to assembled implants, instruments may be conveniently prepared according to the methods of this invention which may be utilized for insertion of other implants. In one embodiment of this invention, therefore, an implant driver is produced wherein the driving mechanism itself is formed from assembled cortical pins which protrude into mating recesses in an implant device. The instrument may be torqued to adequate loads to induce implantation of spinal implants and the like.

In developing the various embodiments of the present invention, one technical issue of merit is the need to develop a process whereby donor tissue, whether hard or soft tissue, allograft or xenograft tissue, may be treated in such a fashion as to eliminate the possibility of cross contamination between tissue segments obtained from different sources. While it is possible to practice the present invention to advantage using tissue obtained from a single screened donor, the real economies of scale and commercially viable application of the present technology is best realized by implementation of an efficient and reliable tissue decontamination process. Ideally, the process is one which permits multiple segments of soft or hard tissue to be treated simultaneously so that a stock of materials for assemblage of implants according to the present invention is facilitated. Accordingly, on preferred method for treatment of tissue, disclosed in PCT publication WO 00/29037, the disclosure of which is hereby incorporated herein by reference as if fully set forth herein (and priority of the U.S. patent filings which gave rise to this application is hereby claimed for that purpose). Accordingly, in this aspect of the invention, a process is claimed whereby an assembled allograft or xenograft tissue implant is prepared by treating the tissue in a closed container in which different cleaning solutions are contacted with the implant segments, either before or after assembly and machining into the final implant form, either in the presence or absence of sonication, with rapid oscillation of pressure in the closed container, to achieve deep cleaning and interpenetration of cleaning solvents into the interstices of porous implants or tissues. Solutions including, but not limited to detergent solutions, peroxide solutions and the like are used in such procedure, and terminal sterilization with gamma irradiation, gaseous sterilants known in the art or other terminal sterilization procedures known in the art are employed to ensure safe implantation of the assembled implants according to this invention.

Referring now to FIG. 1, there is shown a flow-chart representing various elements that may be processed and assembled according to this invention. Cortical bone pins 100 are used to assemble a series of bone disks 101 into a pre-part 102 which is then machined into a series of final products: Threaded dowels, 103; small blocks 104; unique shapes, 105 such as a "wedding-cake" like shape wherein disks bearing threads are spaced apart from each other leaving voids 105' into which additional materials may be inserted, with the disks retained in fixed relation to each other by means of the through pins 100; tapered dowels 106; screws 107; smooth cylinders 108; or large blocks 109. From this figure, it will be appreciated that a central concept relevant to the present invention is the ability to machine smaller parts of tissue, specifically bone tissue, such as cortical bone, cancellous bone, cortical-cancellous bone, portions of which may be demineralized (see, for example, U.S. Pat. No. 6,090,998, hereby incorporated herein by reference for this purpose), and assemble these portions of tissue using, preferably, cortical bone pins. The assembled tissue pieces may be machined prior to assembly, and then, upon assembly, a complete implant is ready for implantation. Alternatively, the tissue pieces may first be assembled, and the assembled pieces may then be machined into any desired final form. The order of assembly and machining will be determined by the specific forms of implant required for a particular application. In FIG. 1, a series of pre-machined tissue forms are disclosed, which may conveniently be included in a kit for use as needed by an orthopedic surgeon. Thus, for example, where a particular implant of specific dimensions is required, the surgeon is able to select pre-shaped implant segments to fill a particular geometric space and shape in the spine of an implant recipient. Numerous permutations and combinations of implant pieces for assembly are possible, based on the pre-machined assemblable implant pieces included in such a kit, and those skilled in the art will appreciate that the skilled orthopedic surgeon will be able to create implants as needed when supplied with such a kit. Thus, a preferred kit includes disks of bone, cortical bone, cancellous bone, allograft or xenograft, also referred to herein as "washers" or "doughnuts" such that a center hole is provided for press-fitting or screwing on of the disks to a cortical bone or synthetic or metallic shaft or pin. The disks may be demineralized, mineralized, or partially demineralized. Also desirable in such a kit are plugs of cortical bone, cancellous bone, or cortical-cancellous bone, including at least one through hole, and optionally more than one such through hole, for insertion of pins therethrough. Ovals, squares, rectangles and irregular shapes may also be provided in certain kits for specific applications. It will further be appreciated, based on the present disclosure, that inclusion of a bone paste, such as that disclosed in WO99/38543, hereby incorporated by reference, may be beneficial for filling any voids that remain, and to implant with the assembled implant, osteogenic material, (i.e. osteoconductive material, Osteoinductive material, or both, as well as material that assists in adhering the implant to the site of implantation). Further, a molded implant may be combined with the assembled implant of this invention. A preferred molded implant for orthopedic applications is disclosed in PCT publication WO 00/54821, the disclosure of which is hereby incorporated by reference.

Figure 2A:
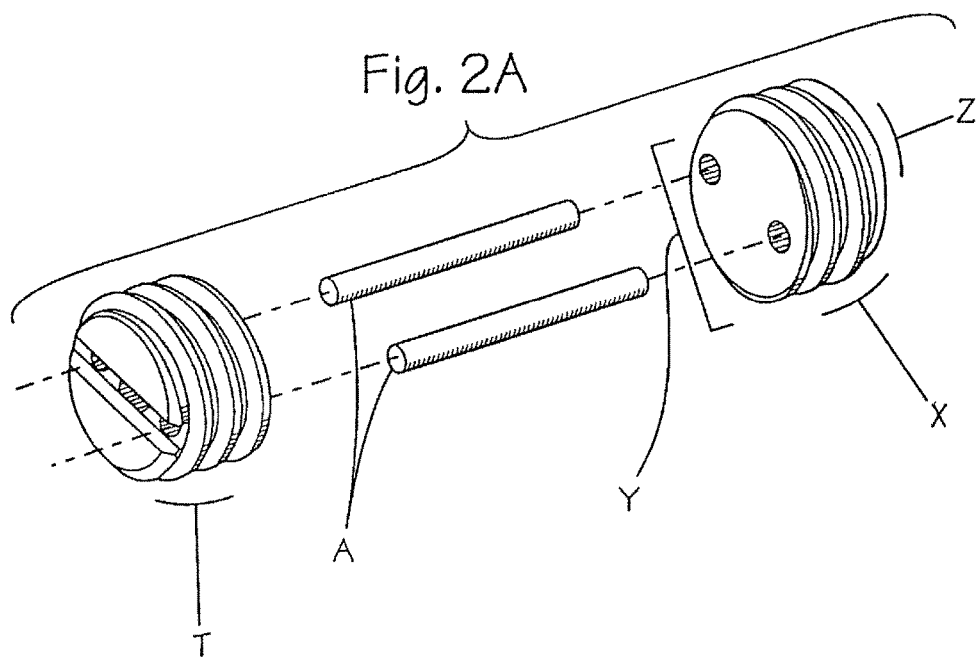
FIG. 2 provides a schematic of an assembled implant according to this invention.
Figure 2B:
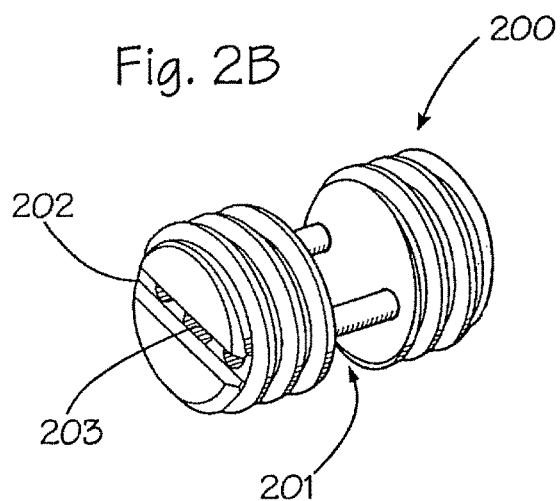
Figure 15:
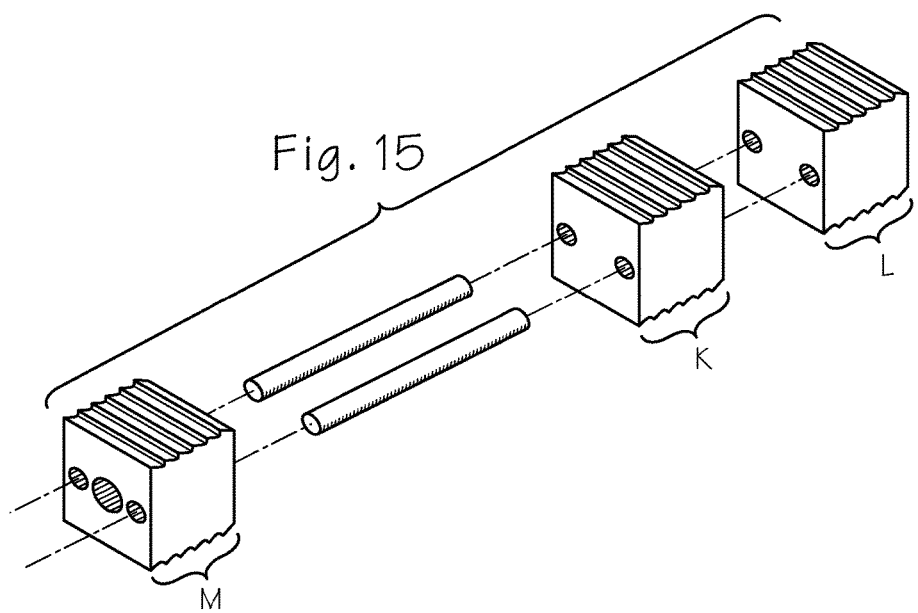
FIGS. 15-18 provides a schematic of an assembled implant according to this invention.
Figure 16:
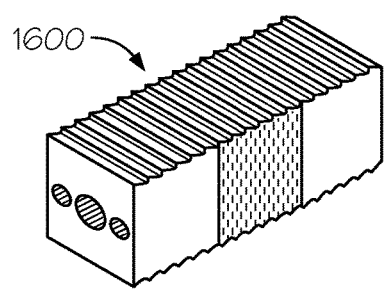

With reference to FIG. 2, there is shown two machined bone pieces, T and Z each of which bear external threading X and holes Y into which pins A are inserted to form the assembled graft 200. As can be seen, the assembled graft 200 comprises a void, 201 into which osteogenic material may be inserted prior to or after implantation. The pins Y may be metal pins, but preferably are pins machined from cortical bone. This enables the entire implant to remodel into autogenous tissue over time, such as vertebral bone, when the implant 200 is inserted into the intervertebral space. The graft 201 is also shown with a groove, 202 in which a driver may be inserted to provide rotational torque for insertion of the implant. An instrument attachment hole, 203, is also provided, to ensure that the implant remains securely on the head of the driver means in the process of surgical implantation. Naturally, those skilled in the art will appreciate that the segments Z and T may be brought into close abutment with each other, thereby eliminating the space 201. In that event, the length of the pins A would be modified to prevent unnecessary protrusion, although in some applications, protrusion may be useful when driving the implant 200 into place. It will also be appreciated that the number of pins used, while represented as two in this figure, may be fewer or more in number, depending on the particular application, the extent of torsional or compressive loads, and the like anticipated to be experienced by the implant once in situ.

FIG. 3 shows an implant assembled from three principal segments F, D, and E, which are held together by pins 300. In this implant, the waffle-shaped structure of implant segment D is intended to represent the use of cancellous bone, which is abutted on either side by cortical bone, which forms segments F and E. The fully assembled implant is shown in FIG. 4, while FIGS. 5, 6 and 7 show end-on views, and cross sectional views A-A and B-B, respectively. Those skilled in the art will appreciate from this disclosure that segment F, segment D, or segment E may be demineralized according to methods known in the art. Likewise, all of these segments may be demineralized. Where a flexible implant is required, the implant may be assembled, and the entire implant may be demineralized.

FIG. 8 shows an embodiment of this invention wherein rectangular bone segments N and G are assembled into implant 900, shown in FIG. 9. Features 901 and 902 which comprises ridges, teeth, or other external features are machined into the superior and inferior faces of the implants in order to assist in retention of the implants once placed in situ.

FIGS. 10-14 show the assembly of elements J, H, and I into implant 1100, shown end-on, in cross-section A-A and B-B, in FIGS. 12-14, respectively. As can be seen, bone element H is shown with a waffle-like structure, to represent that this element may be cancellous bone, demineralized bone, a polymer composite, such as poly-L-Lactic acid, polyglycolic acid, or the like. Features 1101 and 1102 represent external grooves or teeth machined into the superior and inferior surfaces of the implant to assist in retention of the implant once placed in situ.

Figure 17:
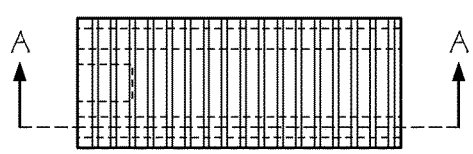
Figure 18:
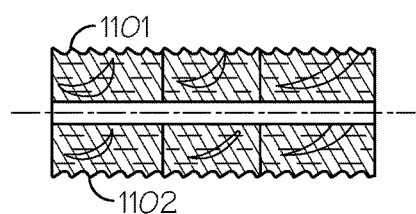

FIGS. 15-18 show the assembly of elements M, K, and L, each of which is a substantially cubic bone element, using pins 1500. FIG. 17 is a top view, showing cross section A-A, represented in FIG. 18, with the final assembled implant 1600 shown in FIG. 16.

Figure 19A:
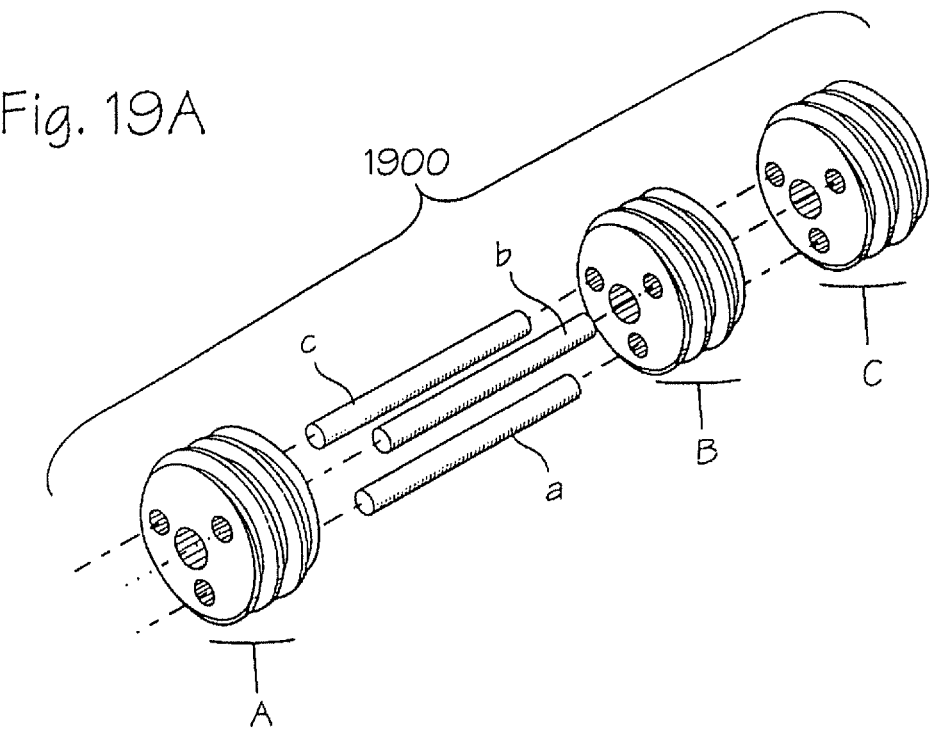
FIG. 19 provides a schematic of an assembled implant according to this invention.
Figure 19B:
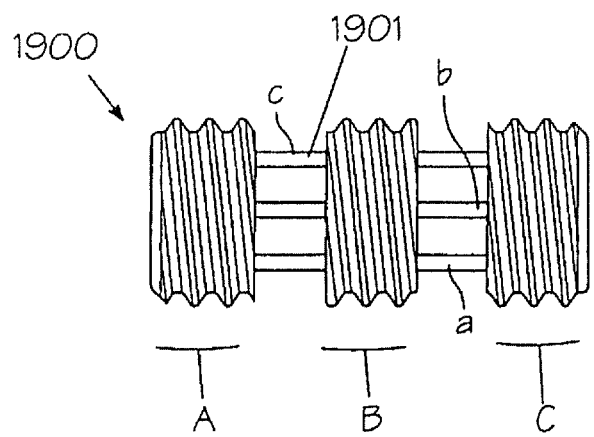
Figure 20A:
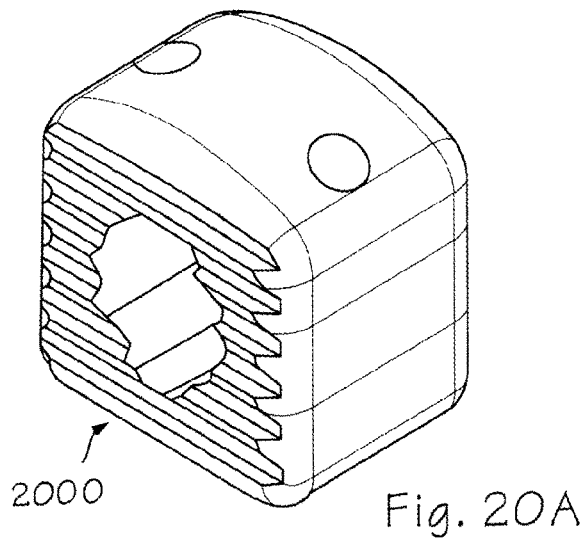
FIG. 20 provides a schematic of an assembled implant according to this invention.
Figure 20E:
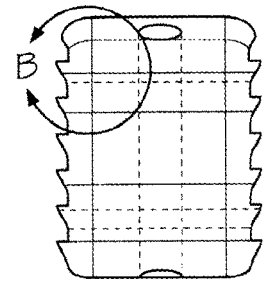
Figure 20B:
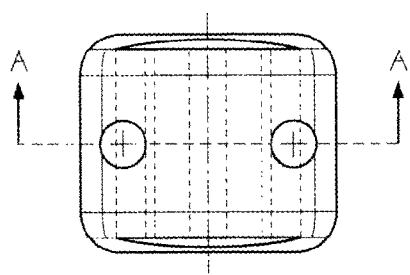
Figure 20F:
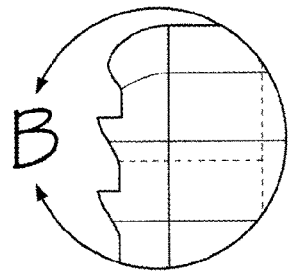
Figure 20C:
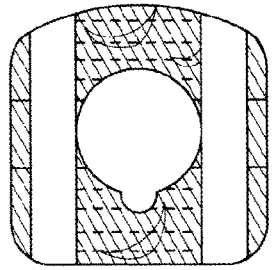
Figure 20D:
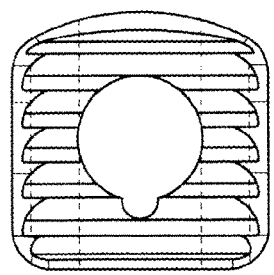
Figure 20G:
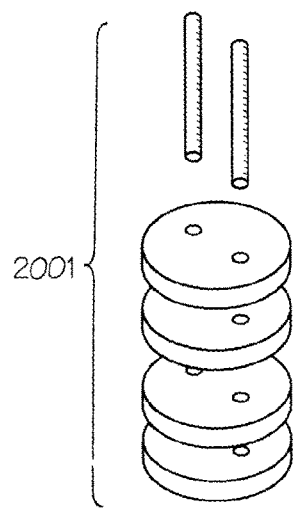
Figure 21A:
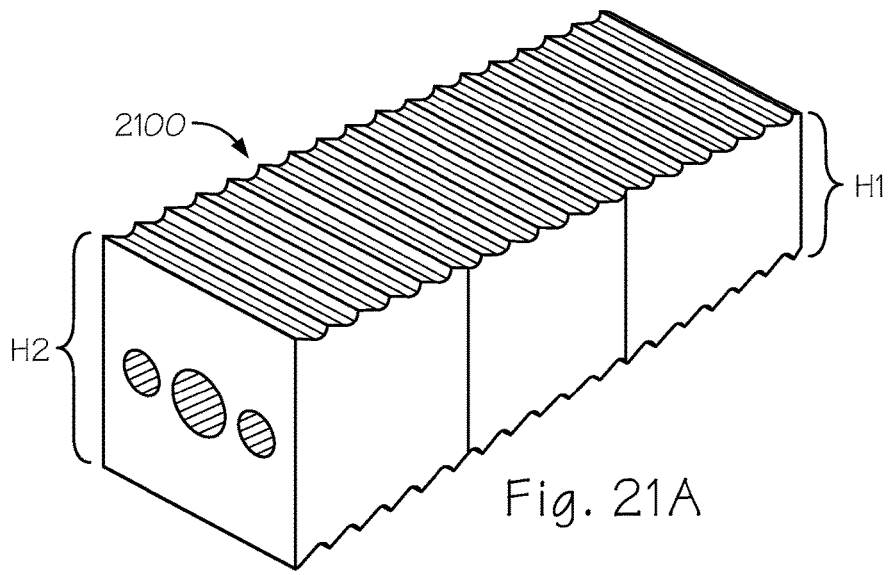
FIG. 21 provides a schematic of an assembled implant according to this invention.
Figure 21B:
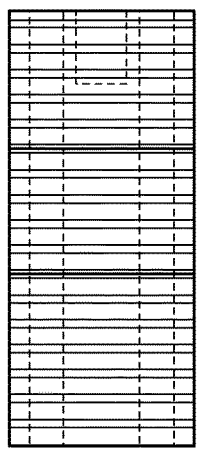
Figure 21C:
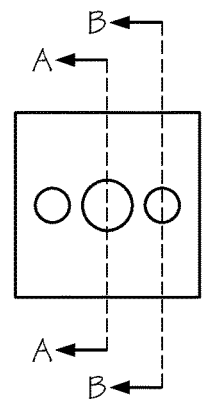
Figure 21D:
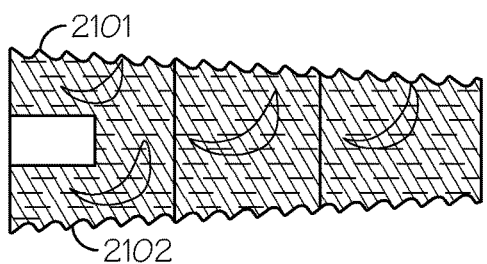
Figure 21E:
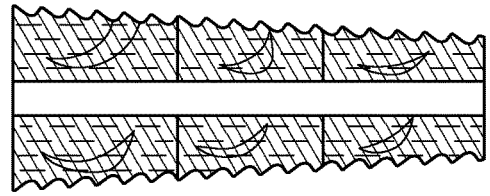

FIG. 19 shows a "Wedding-Cake" design of an implant 1900 assembled from units A-C, pinned together by pins a-c. Void area 1901 is available for filling with osteogenic materials.

FIG. 20 shows implant 2000 which is an assembled Cervical Smith Robinson implant similar to that shown in PCT publication WO99/09914, hereby incorporated by reference, except that this implant is fashioned from a series of assembled bone pieces 2001 and machined into the desired final shape.

FIG. 21 shows implant 2100 assembled from two cortical bone pieces and one cancellous bone piece, and pinned together. The implant has an anterior height 111 which is smaller than posterior height 112, which permits retention of correct spinal lordosis upon implantation, for example, in a posterior lumbar intervertebral implant fixation procedure. Superior and inferior features 2101, 2102 prevent expulsion of the implant once place in situ.

FIG. 22 shows an implant 2200 assembled from a series of sub-implant pieces 2201. The implant may contain cancellous bone 2202 segments, as well as cortical bone 2203 segments and cortical bone pins 2204.

Figure 23:
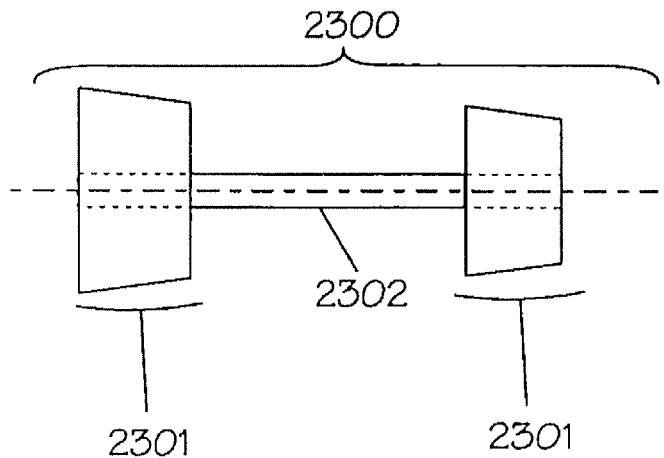
FIG. 23 shows the assembly of a dowel from component pieces.
Figure 24A:
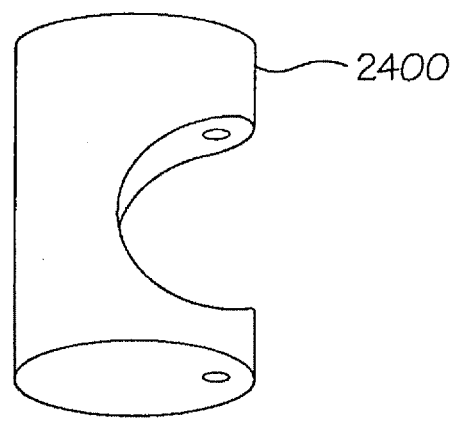
FIG. 24 shows the reinforcement of an implant using a cortical bone pin.
Figure 24B:
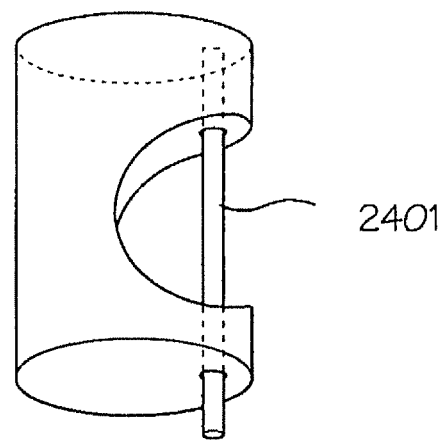

FIG. 23 shows the formation of a tapered dowel 2300 by assembling "doughnut" or "disk" or "washer" shaped bone pieces 2301 on a cortical bone shaft 2302 by using washer pieces of differing diameter. This figure only shows two disks, but a continuous dowel is formed by using disks of a graded diameter between each end of the cortical bone shaft 2302. In FIG. 24, FIG. 24A shows a bone dowel in which one sidewall of a bone dowel 2400 such as that disclosed and claimed in U.S. Pat. No. 5,814,084, hereby incorporated by reference, is "out of specifications" due to being too narrow or absent. This is repaired in FIG. 24B according to this embodiment of the invention by incorporation of an allograft or xenograft cortical bone pin 2401, to form a complete bone dowel. In this manner, valuable biological material which might otherwise be unusable for a particular application may be salvaged for use by employing the methodology of this invention.

Figure 25A:
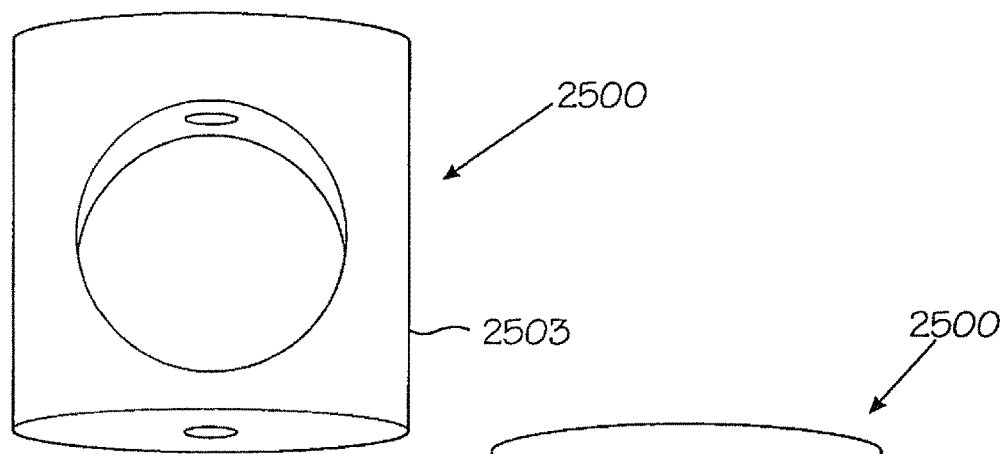
FIG. 25 shows the reinforcement of an implant using a cortical bone pin and a cortical bone disk.
Figure 25B:
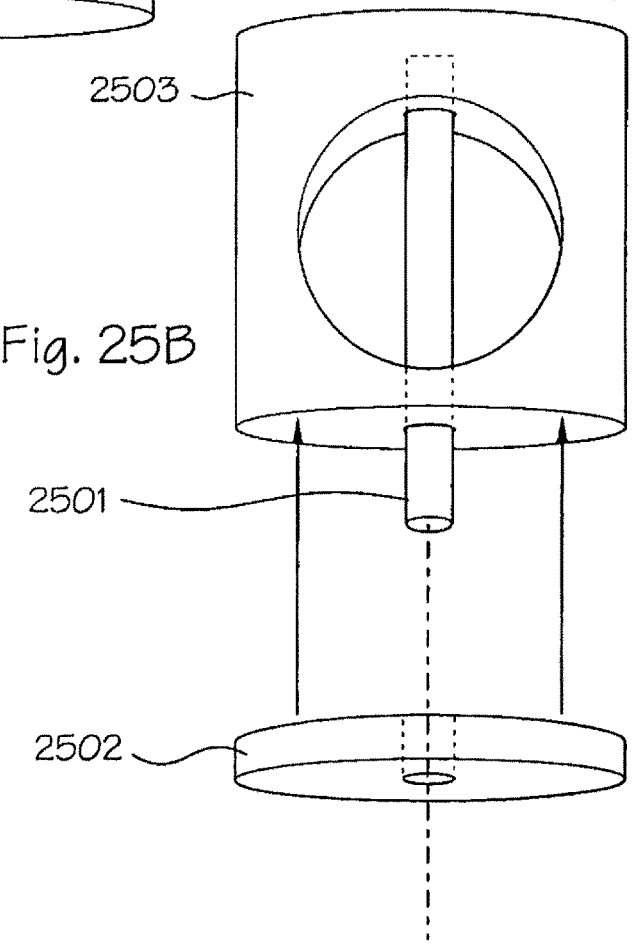
Figure 26A:
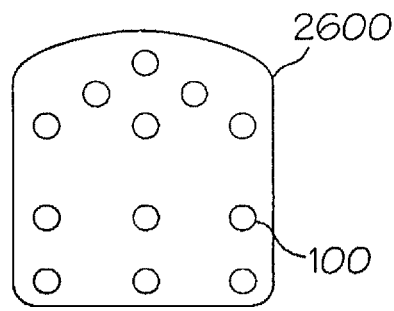
FIG. 26 shows the reinforcement of cancellous bone implants using a plurality of cortical bone pins.
Figure 26B:
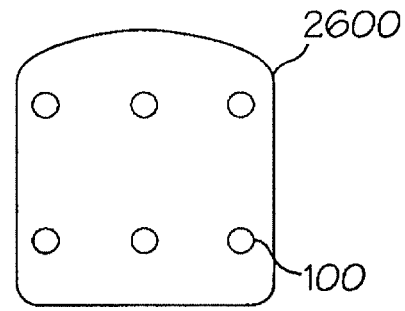
Figure 26C:
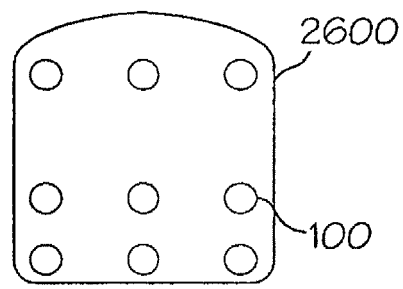
Figure 26D:
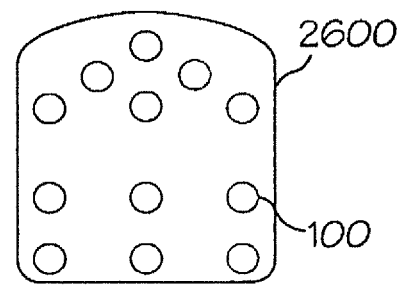
Figure 26E:
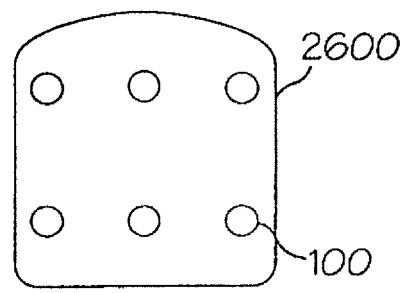
Figure 26F:
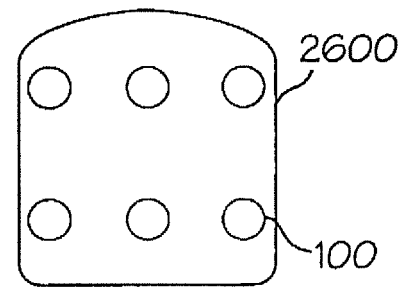

In FIG. 25, a similar procedure for salvaging a dowel 2500 is shown whereby a pin 2501 is driven through the center of the dowel 2500 to reinforce the dowel longitudinally. Furthermore, where an endcap 2503 of the dowel is "out of spec" for being too narrow, the endcap is reinforced by press-fitting a cortical bone disk 2502 onto the end of the pin 2501.

In FIG. 26, a series of cancellous bone implants 2600 are reinforced by inclusion therein of a series of cortical pins 100. Each cortical pin of a 2 mm diameter has been found to support approximately 2000 newtons of axial compressive load. Accordingly, cancellous bone implants of essentially any desired height and compressive strength may be assembled in this manner by affixing several layers of cancellous bone with cortical bone pins. Naturally, based on this disclosure, those skilled in the art will appreciate that other materials may be included in such a "sandwich" of bone materials. The cancellous bone may be soaked in a solution containing growth factors, such as, but not limited to, bone morphogenetic proteins, fibroblast growth factors, platelet derived growth factor, cartilage derived morphogenetic proteins, stem cells, such as mesenchymal stem cells, osteoprogenitor cells, antibiotics, antiinflammatory compounds, anti-neoplastic compounds, nucleic acids, peptides, and the like. Those skilled in the art will also appreciate that layers of cortical bone may be included, layers of biocompatible synthetic polymers and the like may also be included in the stacked bone implant. Various shapes may also be built upon, using for example, circles, ellipses, squares, and the like, as necessary for a given application.

In a further aspect of the present invention, the assembled implant is driven by cortical pins to seat in an implant site, using a driver that engages cortical bone pins with purchase sites on the implant. Thus, for example, not meant to be limiting, the driver may comprise a handle with projecting cortical pins which engage with holes in the assembled allograft, thereby providing a site for torquing the implant into position.

Figure 27:
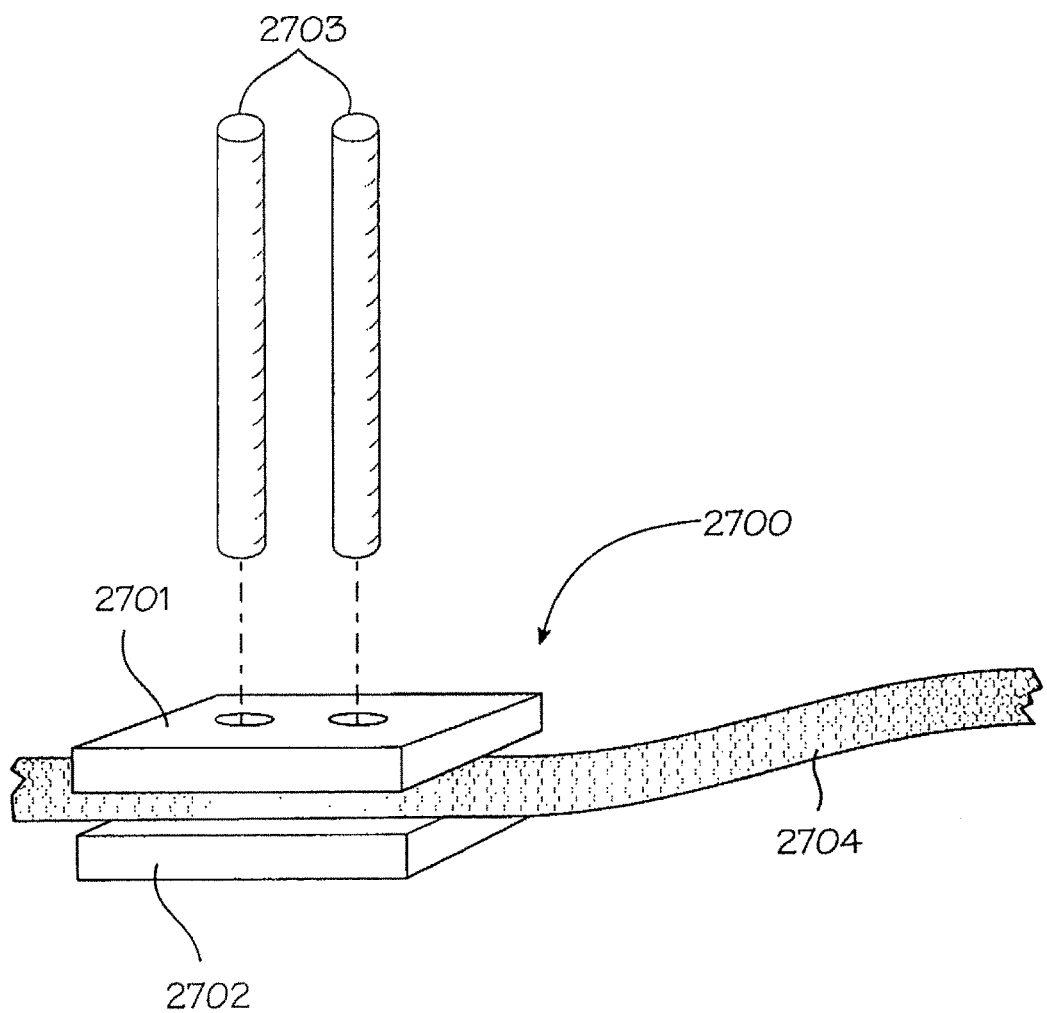
FIG. 27 shows the formation of an assembled implant comprising soft and hard tissues.

In a further embodiment according to this invention, assembled cortical bone blocks, or cortical cancellous bone blocks are assembled in combination with wedged or pinned soft tissue, such as tendon, ligament, skin, collagen sheets, or the like, to create grafts similar to naturally occurring tissue sites, such as the bone-tendon interface found at the patella. Such combination implants permit reconstruction of sites such as the Anterior Cruciate Ligament (ACL) or Posterior Cruciate Ligament (PCL). According to this embodiment of the invention, a ligament or tendon or skin or collagen sheet membrane is pinned between adjacent blocks of cortical bone. Accordingly, various implants, such as known bone-tendon-bone implants which are in short supply may be supplanted by assemblage of an implant comprising assembled bone blocks, between which is fixed a ligamentous tissue, including but not limited to ligament, tendon, demineralized bone, and the like. Referring to FIG. 27, there is shown one example of this embodiment of the present invention in which an implant 2700 is assembled from a superior bone block 2701, an inferior bone block 2702 and a wedged flexible tissue, such as a ligament or tendon or portion of demineralized bone 2704, all of which are pinned together with cortical bone pins 2703 or other fixation means. Naturally, those skilled in the art will appreciate, based on this disclosure, that other shapes of bone blocks, such as rounded bone blocks, and other types of combinations of soft and hard tissues may be assembled according to this disclosure. However, the example of such an implant 2700 may be used instead of having to harvest a bone-tendon-bone implant from cadaveric knees, which tissue is in short supply.

Based on the present disclosure, those skilled in the art will further appreciate that the cortical bone pins disclosed herein may have features defined thereon for various applications. For example, not meant to be limiting, the shafts may contain stops, such that other pieces of bone inserted thereon can only travel a certain distance down the shaft before encountering the stop. The shaft may also contain through holes, to permit insertion of cotter pins or the like. Furthermore, the cortical bone shaft may be demineralized, mineralized, or partially demineralized. In one specific embodiment, the end of the cortical shaft contains a tapped cannulation a short distance into the longitudinal end of the shaft. In this way, a screw may be driven into the cannulation to retain elements inserted over the shaft in association with the shaft. To accommodate the screw, the screw end bearing the cannulation may be partially demineralized, such that upon insertion of the retention screw, the shaft end does not shatter, but expands to accommodate the increasing diameter of the screw as it is driven into the shaft. Naturally, in certain applications, it may be desirable for the cortical pins to be cannulated throughout the longitudinal length thereof. However, care should be taken that this does not unduly weaken the overall compressive or torsional strength of the assembled implant. This may be addressed by including pins that are not cannulated, along with pins that are cannulated. The cannulated pins may be used in combination with sutures or the like, in order to hold an implant in a specific orientation, until fusion with adjacent bone has proceeded to a sufficient extent for the implant to become stable without the sutures.

It will be appreciated from the present disclosure that implants that have classically been fabricated from metals may be fabricated by assembling bone pieces. In addition, a benefit of the assembled graft according to this invention is that the components of the assembled graft can be derived from various anatomical structures, thus circumventing limitations normally resulting from having to obtain a graft from a particular anatomical source of a particular donor. Not only can the components be sourced from different anatomies, but also different donors may yield various components for assembly into a unitary implant. The end result is maximization of the gift of donation and the preservation of precious tissue resources. As noted above, being able to pool tissues from different sources depends, to some significant extent, on the ability to treat portions of tissue harvested from different anatomies or donors so as to prevent any contamination of a recipient with pathological or antigenic agents. A further benefit of the present invention is that different implants with height or width limitations due to the anatomical structures from which the implant has been derived may be pinned together to form implants of essentially any desired dimensions. In this fashion, an inventory of building blocks in combination with the appropriate assembly pins, threaded or unthreaded, is useful to provide implants of essentially any dimensions in the course of given surgical procedure. According to this embodiment of the invention, for example, a cervical Smith-Robinson (CSR) t of any desired height may be produced by attaching two or more existing CSR implants together with cortical bone pins. This is accomplished preferably using two machined CSR's of known height such that when added together, the desired overall height is achieved. The two CSR's are stacked and drill holes are machined through the CSR bodies, following which the cortical bone pins are press-fit through the thus machined holes. Preferably, the diameter of the pins is slightly greater than the diameter of the drilled holes, such that a tight press-fit is achieved.

From the present disclosure, it will further be appreciated that implants according to this invention may be assembled in the operating room by a surgeon, using pre-formed implant pieces, from a kit. It will further be appreciated that the assembled implant pieces may be adhered to each other using any of a number of biologically acceptable glues, pastes and the like. In one such embodiment, the assembled implant pieces are assembled using a polymethyl-methacrylate glue, a cyanoacrylate glue, or any other adhesive known in the art, so long as the use of such an adhesive is confirmed to be non-toxic. It will further be appreciated that in forming the assembled grafts according to the present invention, it is acceptable, although not required, for interlocking features to be included on abutting faces of implant segments to be assembled together. Where such features are included, it is preferred for the adjacent features to be complementary, such that a protrusion on a first surface is met by a compatible indentation in the abutting surface. Such abutting features assist to provide torsional and structural strength to the assembled implant, and to relieve a measure of stress on the cortical bone pins used to assemble the implant.

According to U.S. Pat. No. 6,025,538, an elaborate system is disclosed for ensuring that a bore is provided in mating surfaces of a composite implant such that the bore is angularly aligned with respect to mating surfaces so as to be oblique to the plane of each mating surface. This is not required according to the present invention.

According to U.S. Pat. No. 5,899,939, layers of bone are juxtaposed, but no mechanical fixation of the various layers to each other is provided for, such as the cortical bone pins disclosed herein.

With respect to PCT Publication WO 00/40177 and the priority U.S. patent filings, Ser. No. 09/225,299, filed 5 Jan.

1999, Ser. No. 09/286,975, filed 6 Apr. 1999, and Ser. No. 09/368,263, filed 3 Aug. 1999, it is believed that there exists interfering subject matter claimed in the present and in those applications. As to the interfering subject matter, claims are presented herein which are believed to constitute the basis for initiation of an interference proceeding in the United States, and initiation of such a proceeding is hereby specifically elicited, in which it is believed that the present applicants are entitled to priority. As to the non-interfering subject matter disclosed and claimed herein, the right to file one or more continuation or divisional applications free of interfering subject matter is reserved.

Having generally described this invention, including the methods of manufacture and use thereof, including the best mode thereof, those skilled in the art will appreciate that a large number of variations on the principles described herein may be accomplished. Thus, the specifics of this description and the attached drawings should not be interpreted to limit the scope of this invention to the specifics thereof. Rather, the scope of this invention should be evaluated with reference to the claims appended hereto.

What is claimed is:

1. An assembled bone graft, said assembled bone graft assembled outside the body and suitable for implantation into a human patient, said assembled bone graft comprising:
   (a) two machined allograft bone pieces and an internal piece, wherein:
      i) said machined allograft bone pieces comprise cortical bone;
      ii) said internal piece comprises osteogenic material;
      iii) patterned external grooves or teeth that are machined into superior and inferior surfaces of the graft and traverse each of said machined allograft bone pieces; and
   (b) biocompatible pins consisting essentially of cortical bone, wherein each biocompatible pin completely traverses said graft for holding said graft together as an assembled bone graft; and
   wherein said two machined allograft bone pieces have drilled holes that completely traverse said two machined allograft bone pieces, and said biocompatible pins are press-fit in said drilled holes across the entire length of said drilled holes.

2. The graft of claim 1 wherein two biocompatible pins are used.

3. The graft of claim 1 wherein the interface between said two machined allograft bone pieces is substantially planar.

4. The graft of claim 1 wherein said osteogenic material comprises allograft bone, autograft bone, demineralized bone, bone powder, bone derivatives, bone morphogenetic protein, antibiotics, bioactive glass, hydroxyapatite, bioactive ceramics, or combinations thereof.

5. An assembled bone graft comprising machined allograft bone having a substantially "D"-shaped external profile, wherein said assembled bone graft is made from stacked machined allograft bone pieces;
   wherein said stacked machined allograft bone pieces comprise substantially planar faces that are substantially parallel to each other; and
   wherein said stacked machined allograft bone pieces are stacked on top of or adjacent to each other and are pinned to each other using biocompatible pins; and
   wherein said machined allograft bone pieces have drilled holes that completely traverse said machined allograft bone pieces, and said biocompatible pins are press-fit in said drilled holes across the entire length of said drilled holes; and wherein said biocompatible pins consist essentially of cortical bone, and each biocompatible pin completely traverses said graft, holding said graft together as an assembled bone graft.

6. An assembled bone graft comprising machined allograft bone having a substantially "D"-shaped external profile, wherein said assembled bone graft is made from two machined allograft cortical bone pieces and wherein said machined allograft cortical bone pieces comprise:
   i) a substantially straight rear wall
   ii) a substantially straight side wall; and
   iii) a curved front wall
   and further wherein said machined allograft bone pieces are stacked on top of or adjacent to each other to form said assembled bone graft; and
   wherein said machined allograft bone pieces are held together utilizing biocompatible pins and said machined allograft bone pieces have drilled holes that completely traverse said machined allograft bone pieces, and said biocompatible pins are press-fit in said drilled holes across the entire length of said drilled holes; and wherein said biocompatible pins consist essentially of cortical bone, and each biocompatible pin completely traverses said graft, holding said graft together as an assembled bone graft.

7. The graft of claim 1, wherein said biocompatible pins are impelled through each piece of said assembled bone graft such that the implants are formed into a unitary body by said biocompatible pins.

8. The graft of claim 5, wherein said biocompatible pins are impelled through each of said machined allograft bone pieces such that the implants are formed into a unitary body by said biocompatible pins.

9. The graft of claim 6, wherein said biocompatible pins are impelled through each piece of said assembled bone graft such that the implants are formed into a unitary body by said biocompatible pins.

10. The graft of claim 6, wherein said machined allograft bone pieces comprise two mirror image halves of a desired shape.

11. The graft of claim 6, further comprising patterned external grooves or teeth that are machined into superior and inferior surf aces of the graft and traverse each of said machined allograft bone pieces.

12. An assembled bone graft comprising machined allograft
   bone, wherein said assembled bone graft is made from stacked machined allograft bone pieces; wherein said stacked machined allograft bone pieces comprise substantially planar faces that are substantially parallel to each other; and
   wherein said stacked machined allograft bone pieces are stacked on top of or adjacent to each other and are pinned to each other using biocompatible pins; and
   wherein said machined allograft bone pieces comprise discontinuous walls consisting substantially of cortical bone and wherein said discontinuous walls comprise mirror image halves which, in combination, comprise the shape of the graft; and
   wherein said machined allograft bone pieces have drilled holes that completely traverse said machined allograft bone pieces, and said biocompatible pins are press-fit in said drilled holes across the entire length of said drilled holes; and wherein said biocompatible pins consist essentially of cortical bone, and each biocompatible pin completely traverses said graft, holding said graft together as an assembled bone graft.

13. An implant comprising at least two shaped cortical bone implants stacked on top of or adjacent to each other, wherein said shaped cortical bone implants are adapted to form a unitary implant for implantation into an appropriately dimensioned cavity formed between adjacent vertebrae and wherein said at least two cortical bone implants are pinned to each other by cortical bone pins; and wherein said shaped cortical bone implants have drilled holes that completely traverse said shaped cortical bone implants, and said cortical bone pins are press-fit in said drilled holes across the entire length of said shaped cortical bone implants; and wherein each said cortical bone pins completely traverses said implant, holding said implant together.

14. The graft of claim 13, wherein said cortical bone pins are impelled through each piece of said shaped cortical bone implants such that the final implant is formed into a unitary body by said biocompatible pins.

15. The implant of claim 13, wherein said shaped cortical bone implants are two mirror image halves of a desired shape.

16. The implant of claim 13, wherein a single unitary implant composed of said shaped cortical bone implants can be produced having a desired height.

* * * * *